United States Patent [19]
Baykut

[11] Patent Number: 5,981,600
[45] Date of Patent: Nov. 9, 1999

[54] HYDROXYANTHRAQUINONE DERIVATIVES

[76] Inventor: Fikret Baykut, Ataköy, 1. Kisim, Blok D-1, Daire 2, Istanbul, Turkey

[21] Appl. No.: 08/918,794

[22] Filed: Aug. 26, 1997

[30] Foreign Application Priority Data

Sep. 2, 1996 [DE] Germany .......................... 196 35 557

[51] Int. Cl.$^6$ .................................................. A01N 33/02
[52] U.S. Cl. ......................... 514/656; 552/247; 552/248; 564/196
[58] Field of Search ........................... 514/636; 564/196; 552/248

[56] References Cited

U.S. PATENT DOCUMENTS

| | | | |
|---|---|---|---|
| 4,197,249 | 4/1980 | Murdock et al. | 260/380 |
| 4,310,666 | 1/1982 | Zee-Cheng et al. | 544/380 |
| 4,732,970 | 3/1988 | Fields et al. | 530/323 |
| 4,888,137 | 12/1989 | Murdock et al. | 552/248 |

FOREIGN PATENT DOCUMENTS

| | | |
|---|---|---|
| 85109732 | 8/1985 | European Pat. Off. . |
| 87108677 | 6/1987 | European Pat. Off. . |

OTHER PUBLICATIONS

Solomon's, "Organic Chemistry, 3rd Edition", pp. 1020–1026, 1984.

"Antineoplastic Agents. Structure–Activity Relationship Study of Bis(substituted aminoalkylamino)anthraquinones," R.K.Y. Zee–Cheng and C.C. Cheng, Journal of Medicinal Chemistry, 1978, vol. 21, No. 3, pp. 291–294.

"Antitumor Agents. 1. 1,4–Bit[(aminoalkyl)amino]–9, 10–anthracenediones," K.C. Murdock, R.G. Child, P.F. Fabio, R.B. Angier, R.E. Wallace, F.E. Durr, and R.V. Citarella, Journal of Medicinal Chemistry, 1979, vol. 22, No. 9, pp. 1024–1030.

"Failure of the Electron Transfer Mechanism in Cancer Development," F. Baykut, D. Baykut, and G. Baykut, International Journal of Experimental and Clinical Chemotherapy, vol. 2, No. 2, 1989, pp. 76–86.

Primary Examiner—Dwayne C. Jones
Attorney, Agent, or Firm—Blakely, Sokoloff, Taylor & Zafman

[57] ABSTRACT

A compound selected from the group having the general formula

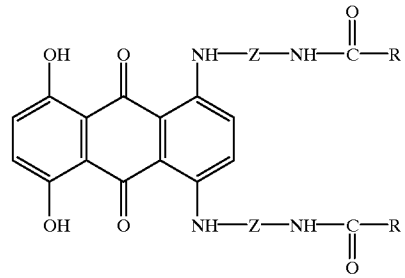

wherein Z is a divalent moiety selected from linear or branched, saturated or unsaturated alkylene group, and the O=C(R) group contains one of a quaternary ammonium group and a sugar moiety, or the O=C(R) group is part of a neuraminic acid moiety, and their pharmacologically acceptable acid addition salts. Also a medical preparate with antineoplastic effects utilizing such a compound.

8 Claims, No Drawings

HYDROXYANTHRAQUINONE DERIVATIVES

SUMMARY

The invention is about a series of novel symmetric amides of 1,4-bis-substitued alkylenediamino-5,8-dihydroxyanthraquinones with various monocarboxylic acid, which exist in the human organism, as well as other monocarboxylic acids, which can be obtained from substances, which exist in the human organism. These monocarboxylic acids are among others those, which contain a quaternary ammonium group, like for instance 3-hydroxybutyric acid-4-trimethylammoniumchloride (carnitine chloride) and Acetic acid trimethylammonium chloride, an oxidation product of choline, the N-acetyl neuraminic acid, as well as monocarboxylic derivatives of various sugar molecules, for example gluconic acid or 2-amino gluconic acid.

BACKGROUND OF THE INVENTION

1. Field of the Invention

The invention is about a series of novel symmetric amides of 1,4-bis-substituted alkylenediamino-5,8-dihydroxyanthraquinones with various monocarboxylic acid, which exist in the human organism, as well as other monocarboxylic acids, which can be obtained from substances, which exist in the human organism. These monocarboxylic acids are, among others, those which contain a quaternary ammonium group, like for instance 3-hydroxybutyric acid-4-trimethylammoniumchloride (carnitine chloride) and acetic acid trimethylammonium chloride, an oxidation product of choline, the N-acetyl neuraminic acid, as well as monocarboxylic derivatives of various sugar molecules, for example gluconic acid or 2-amino gluconic acid.

2. Description of the Related Art

About three decades ago, the first anthracycline antibiotics were obtained through biological synthesis by fungus *Streptomyces paucetius* var. *caesius*. As described in the classical reference book by A. Goodman Gilman, L. S. Goodman, T. W. Rall, F. Murad, "Goodman Gilman's Pharmaceutical Basis of Therapeutics", 7th edition, McMillan Publishing Company, New York, 1985, pp 1283, anthracycline antibiotics and their derivatives show a very strong antitumor activity. One representative of this group is daunorubicine. It was isolated independently by both DiMarco and Dubost et al. in 1963. A very similar compound is the doxorubicine. It was first isolated in 1969 by Arcamone. Although these two compounds are very similar in structure, daunorubicine is primarily used in acute leukemias while doxorubicine is applied against a wide range of human neoplasms including solid tumors.

However both of these compounds showed also toxic effects to the organism (Goodman Gilman's Pharmaceutical Basis of Therapeutics, 7th edition, 1985), and can cause, depending on the dose applied, an often irreversible cardiomyopathia. Following the invention of the first anthracycline antibiotics, several anthracycline derivatives were prepared and tested in order to find an alternative compound with high antitumor activity, but at the same time with reduced cardiac toxicity. Mitoxantrone, a synthetically obtained compound, is one of these antitumor agents. It is an aminoanthracenedione (1,4-bis[2-(2-hydroxyethylamino) ethylamino]5,8-dihydroxyanthraquinone hydrochloride) and is used very frequently against various neoplastic developments in human organism. The U.S. Pat. No. 4,197,249 from 1980 is about a series of substituted anthraquinone derivatives, including mitoxantrone.

The scientific publications of Zee-Cheng and Cheng (R. K.-Y. Zee-Cheng, C. C. Cheng, "Antineoplastic agents. Structure-reactivity relationship study of bis (substituted aminoalkylamino) anthraquinones, Journal of Medicinal Chemistry, volume 21, year 1978, pages 291–294) and of Murdock et al. (K. C. Murdock, R. G. Child, P. F. Fabio, R. B. Angier, R. E. Wallace, F. E. Durr, R. V. Citarella, "Antitumor agents. 1. 1,4-Bis[(aminoalkyl)amino]-9,10-anthracenediones", Journal of Medicinal Chemistry, Volume 22, year 1979, pages 1024–1030) report about various compounds of this class.

BRIEF DESCRIPTION OF THE INVENTION

It is the objective of the invention, to synthetise new hydroxyanthraquinone derivatives, which show a very strong antineoplastic activity and using which medicines can be produced that are appropriate for chemotherapeutic treatment of cancerous diseases.

The idea of the invention is, to combine derivatives of 1,4-bis-substituted alkylenediamino-5,8-dihydroxyanthraquinone through amide bond with acyl groups of monocarboxylic acid, which contain a quaternary ammonium groups, or with monocarboxylic acids, which are derivatives of various sugar molecules, or with acyl groups of monocarboxylic acids which are N-acetyl neuraminic acid or its derivatives. These acyl groups are derived from monocarboxylic acids, which exist in the human organism, or can be derived from compounds that exist in the human organism. A hydroxyanthraquinone derivative with these groups will then show a strong antineoplastic effect, since by these appropriate substituents, even very small amounts of this compound will be transferred into the cancerous cells as well as into the mitochondria, where the malignant transformation of the deoxyribonucleic acid begins.

DETAILED DESCRIPTION OF THE INVENTION

This invention is about a new series of organic compounds and particularly the symmetric amides of the 1,4-bis substituted amino-5,8-dihydroxyanthraquinones with carboxylic acids, which may be represented by the following formula

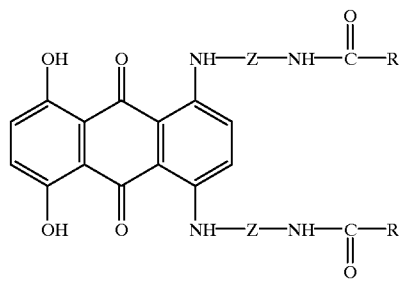

wherein Z is a divalent moiety consisting of a linear or branched, saturated or unsaturated alkylene group. The

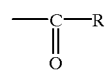

is the acyl group of various monocarboxylic acids that exist in the human organism, or a monocarboxylic acid, which can be obtained by a reaction from compounds that exist in the human organism, as well as pharmacologically acceptable acid addition salts of them. These monocarboxylic acids should contain quaternary ammonium groups, or should be derived by reactions from sugar molecules, or are neuraminic acid or N-acetyl neuraminic acid, or derivatives of these.

The novel compounds of the present invention may be prepared in accordance with the following reaction scheme:

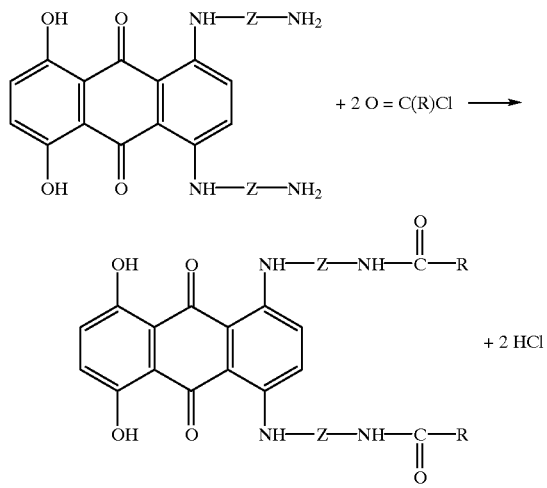

wherein the Z and the R groups are as hereinabove defined. According to the reaction scheme above, 1,4-Z-diamino-5, 8-dihydroxy anthraquinone reacts with the appropriate acid chloride O=C(R)Cl in a solvent such as 2-methoxyethanol at temperatures from about 40° C. to about 55° C. under nitrogen atmosphere for about 10 hours. The solution obtained is filtered. After addition of a sufficient amount of diethyl ether, a precipitate forms. The precipitated product is recrystallized in a water/ethanol system.

This class of compounds have light to dark-blue colored crystals, have characteristic melting points and characteristic absorption spectra. The crystals are soluble in water and in organic solvents like 2-methoxyethanol, but insoluble in diethylether, acetone and ethanol. Through addition of acids, ammonium salts of these series of compounds can be formed, if, for example, the acyl group in the formula contains amino or substituted amino groups.

The use of these compounds will be through the production of medical preparates for parenteral, enteral, oral, cutane or mucosal application with antineoplastic effect.

EXAMPLE 1

1,4-bis-N-carnityl ethylenediamino-5,8-dihydroxyanthraquinone dichloride: 0.712 g (0.002 mol) 1,4-bis-ethylenediamino-5,8-dihydroxyanthraquinone is dissolved in approximately 130 mL 2-methoxyethanol. The solution is stirred in a reactor for 1–2 hours under nitrogen atmosphere at 40° C. and filtered afterwards. 0.8648 g carnitine chloride is added to the filtrate and allowed to stand approximately 12 hours under the same conditions. The mixture is then filtered and 500 mL of diethylether is added to the filtrate and is left for 45 minutes for precipitation. The precipitate is filtered through a glass filter, washed with diethylether, dried at 40° C. and recrystallized from water/ethanol mixture at 4° C. for 12 hours. The product is centrifuged and washed with diethylether and ethanol dried at 40° C. and then in a desiccator over $P_2O_5$ overnight. The melting point is 170–173° C. The obtained compound is soluble in water and in 2-methoxyethanol.

According to preliminary in vitro experiments, this compound shows a very strong anti-tumor activity. After a 48-hour treatment of L1210 leukemia cells show 0.59±0.18 μg/mL of this compound the same activity as 6.90±2.28 μg/mL of the standard comparison substance FCE 24517. This demonstrates that the 1,4-bis-(N-carnitinechloride)-ethylenediamino-5,8-dihydroxyanthraquinone dichloride approximately 12 times stronger acts than the standard comparison substance FCE 24517 for the treatment of the leukemia cells L1210.

EXAMPLE 2

1,4-bis-N-(N-trimethylamino acetyl)-ethylenediamino-5, 8-dihydroxy anthraquinone dichloride: 0.712 g (0.002 mol) 1,4-bis-ethylenediamino-5,8-dihydroxy anthraquinone is dissolved in 350 mL 2-methoxyethanol under nitrogen atmosphere at 40° C. for an hour. 0.688 g (0.004 mol) acetic acid trimethyl ammonium chloride is immediately added to this solution. The mixture is continuously stirred under nitrogen atmosphere for 24 hours at 40° C. and then filtered through a glass filter. 8mL diethyl ether is added to the solution and it is allowed to stand for 45 minutes. The precipitate is then filtered through a glass filter and dried. It is crystallized from water/absolute ethanol solution at 60° C. in a water bath and finally left in at 4° C. for 12 hours. After three recrystallizations, the melting point was 222–226° C. The product consists of dark blue crystals and is soluble in water and 2-methoxyethanol.

EXAMPLE 3

1,4-bis-N-gluconyl ethylenediamino-5,8-dihydroxy anthraquinone: 120 mL 2-methoxyethanol is added to 0.712 g 1,4-bis-ethylenediamino-5,8-dihydroxyanthraquinone and stirred at 40° C. for about an hour. After filtration, the filtrate is transferred into a reactor. 0.858 g gluconic acid chloride is added to the filtrate. This solution is left for about 12 hours under nitrogen atmosphere at 40° C. After cooling down, 500 mL diethylether is added to the product and after 30 minutes it is filtered through a glass filter, washed with diethylether, and dried at 35° C. in a desiccator over $P_2O_5$ for about 12 hours. After three recrystallizations, 1.0 g dark blue crystals are obtained. The melting point is 210–215° C. The obtained compound is soluble in water and in 2-methoxyethanol.

According to preliminary in vitro experiments, this compound shows a very strong anti-tumor activity. After a 48-hour treatment of L1210 leukemia cells show 1.16±0.25 μg/mL of this compound the same activity as 6.90±2.28 μg/mL of the standard comparison substance FCE 24517. This demonstrates that the 1,4-bis-(N-gluconyl)-ethylenediamino-5,8-dihydroxy anthraquinone acts approximately 6 times stronger than the standard comparison substance FCE 24517 for the treatment of the leukemia cells L1210.

Other in-vitro experiments, in particular with leukemia, small cell bronchial carcinoma and renal neoplasm show that a microgram level application of this compound the malignant growth is stopped. A reduction of malignant cells is observed by using higher concentrations.

Experiments with rats showed that the cardiac toxicity of this compound is about one third of the cardiac toxicity of the compound mitoxantrone.

EXAMPLE 4

1,4-bis-N-(2-aminogluconyl)-5,8-dihydroxy anthraquinone: 0.712 g (0.002 mol) 1,4-bisethylenediamino-5,8-dihydroxyanthraquinone is dissolved in 350 mL 2-methoxyethanol under nitrogen atmosphere at 40° C. for an hour. 1.4 g (0.004 mol) 2-aminogluconic acid chloride is immediately added to this solution. The mixture is continuously stirred under nitrogen atmosphere for 24 hours at 40° C. and then filtered through a glass filter. 8 mL diethyl ether is added to the solution and it is allowed to stand for 45 minutes. The precipitate formed is then filtered through a glass filter and dried. It is crystallized from water/absolute ethanol solution at 60° C. in a water bath and finally left at 4° C. for 4 hours. The product consists of dark blue crystals and is soluble in water and 2-methoxyethanol.

EXAMPLE 5

1,4-bis-N-acetyl neuraminyl ethylene diamino-5,8-dihydroxy anthraquinone: 130 mL 2-methoxyethanol is added to 0.712 g (0.002 mol) 1,4-bis-ethylenediamine-5,8-dihydroxyanthraquinone, stirred and filtered. The filtrate is transferred into a glass reactor. 1.311 g (0.004 mol) dried N-acetyl neuraminic acid chloride is immediately added to the mixture. The mixture is continuously stirred under the inert nitrogen atmosphere for 48 hours at about 15° C. It is crystallized from water/ethanol solution (1:9 vol. ratio) and is left at 4° C. for 12 hours. The mixture is filtered through a glass filter and dried in a desiccator over phosphorus pentoxide. After recrystallization, the desired product is obtained as dark-blue crystals. M.P. 86–90° C. It is soluble in water and 2-methoxyethanol.

I claim:

1. A compound selected from the group having the general formula

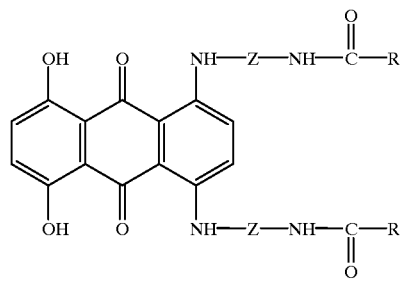

wherein Z is a divalent moiety selected from linear or branched, saturated or unsaturated alkylene group, and the O═C(R) contains one of a quaternary ammonium group wherein each of the four ligands bonded directly to a nitrogen of the quaternary ammonium group are other than hydrogen and a monosaccharide moiety, or the O═C(R) group is part of a neuraminic acid moiety, and their pharmacologically acceptable acid addition salts.

2. The compound of claim 1, wherein R consists of 2-hydroxy-3-N-trimethylammonium chloride-propyl.

3. The compound of claim 1, wherein R consists of N-trimethyl ammoniumchloride-methyl.

4. The compound of claim 1, wherein R consists of 1,2,3,4,5-pentahydroxy-pentyl.

5. The compound of claim 1, wherein R consists of 1-amino-2,3,4,5-tetrahydroxy pentyl.

6. The compound of claim 1, wherein the O═C(R) is O═C(CH$_2$CH(OH)CH(NHCOCH$_3$)CH(OH)CH(OH)CH(OH)CH$_2$(OH)).

7. Medical preparate with antineoplastic effects containing at least a compound selected from the group having the following general formula:

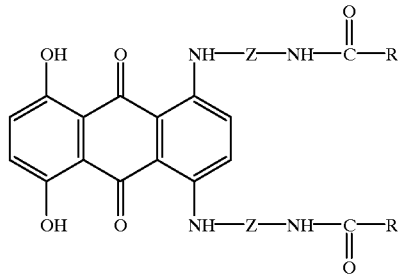

wherein Z is a divalent moiety selected from linear or branched, saturated or unsaturated alkylene group, and the O═C(R) group contains one of a quaternary ammonium group wherein each of the four ligands bonded directly to a nitrogen of the quaternary ammonium group are other than hydrogen and a monosaccharide moiety, or the O═C(R) group is part of a neuraminic acid moiety, and their pharmacologically acceptable acid addition salts.

8. Medical preparate of claim 7 in a form which is appropriate for a parenteral, enteral oral, cutane or mucosal application.

* * * * *